US00PP27431P3

(12) United States Plant Patent
Klemm et al.

(10) Patent No.: US PP27,431 P3
(45) Date of Patent: Nov. 29, 2016

(54) ***PETUNIA* PLANT NAMED 'KLEPH14249'**

(50) Latin Name: *Petunia hybrida*
Varietal Denomination: KLEPH14249

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 95 days.

(21) Appl. No.: 14/545,075

(22) Filed: Mar. 23, 2015

(65) Prior Publication Data

US 2016/0286703 P1 Sep. 29, 2016

(51) Int. Cl.
*A01H 5/02* (2006.01)

(52) U.S. Cl.
USPC ..... Plt./356.23

(58) Field of Classification Search
USPC ..... Plt./356.1, 356.23
See application file for complete search history.

*Primary Examiner* — Susan McCormick Ewoldt

*Assistant Examiner* — Karen Redden

(74) *Attorney, Agent, or Firm* — Barbara Campbell; Bethany R. Roahrig; Cochran Freund & Young, LLC

(57) ABSTRACT

A new *petunia* plant particularly distinguished by having a dark orange flower color and a semi-trailing plant habit, is disclosed.

1 Drawing Sheet

Genus and species: *Petunia hybrida.*
Variety denomination: 'KLEPH14249'.

BACKGROUND OF THE NEW PLANT

The present invention comprises a new and distinct variety of *petunia*, botanically known as *Petunia hybrida*, and hereinafter referred to by the variety name 'KLEPH14249'. 'KLEPH 14249' originated from a controlled-cross between the female *petunia* variety commercially known as Surprise Orange Twist (patent status unknown) and the proprietary male *petunia* variety 'PH-2009-1404', also known as 'KLEPH12216' (unpatented).

In July 2010, two *petunia* parental lines, the female variety Surprise Orange Twist and the male *petunia* variety 'PH-2009-1404' were crossed via a controlled cross in Latina, Italy and seeds were obtained. The seeds were sown and plants were grown for evaluation. A plant line was selected in April 2011 which had a dark orange flower color and was subsequently named 'KLEPH14249'. In April 2011, 'KLEPH14249' was first vegetatively propagated by terminal tip cuttings in Latina, Italy. 'KLEPH14249' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Dark orange flower color; and
2. A semi-trailing plant habit.

DESCRIPTION OF THE PHOTOGRAPH

This new *petunia* plant is illustrated by the accompanying photograph which shows a close-up of the flowers. The photograph is of a four-month-old plant grown outdoors in Stuttgart, Germany in July 2013. The colors shown are as true as can be reasonably obtained by conventional photographic procedures.

DESCRIPTION OF THE NEW VARIETY

The following detailed descriptions set forth the distinctive characteristics of 'KLEPH14249'. The data which define these characteristics were collected from asexual reproductions carried out in Latina, Italy. Data was collected on twelve-week-old plants grown in plastic greenhouse in Latina, Italy in February 2015. Color references are to The R.H.S. Colour Chart of The Royal Horticultural Society of London (R.H.S.), 5$^{th}$ edition (2007).

Classification:
- *Family.*—Solanaceae.
- *Species.—Petunia hybrida.*
- *Common name.—Petunia.*
- *Variety.*—'KLEPH14249'.

Parentage:
- *Female.*—Commercial line Surprise Orange Twist.
- *Male.*—Proprietary male *petunia* 'KLEPH12216'.

Plant description:
- *Form.*—Medium growing.
- *Habit.*—Semi-trailing.
- *Height (from top of soil).*—6.5 cm.
- *Width.*—14.0 cm.
- *Propagation.*—Terminal tip cuttings.
- *Time to produce a finished flowering plant.*—About 14 weeks in winter under short day conditions; 7 weeks in spring.
- *Time to initiate and develop roots.*—2 to 3 weeks.
- *Root description.*—Moderate density, moderate branching, white roots.

Stems:
- *Average number (basal).*—6.
- *Length of basal branches (from the base of the stem to the tip).*—About 8.0 cm.

*Internode length.*—0.3 cm to 1.0 cm.
*Diameter of branches* (*from midpoint*).—0.5 cm.
*Stem color.*—RHS 144C.
*Anthocyanin.*—Absent.
*Texture.*—Tomentose.

Leaves:
*Arrangement.*—Alternate.
*Length.*—About 3.0 cm.
*Width.*—2.2 cm.
*Shape.*—Ovate.
*Apex.*—Broadly acuminate.
*Base.*—Attenuate.
*Margin.*—Entire.
*Immature leaf color.*—Upper surface: RHS 137B. Lower surface: RHS 146B.
*Mature leaf color.*—Upper surface: RHS 137A. Lower surface: RHS 146B.
*Texture* (*both surfaces*).—Tomentose.
*Venation pattern.*—Arcuate.
*Venation color.*—Upper surface: RHS 146C. Lower surface: RHS 146B.
*Petioles.*—Length: 0.3 cm to 0.8 cm. Diameter: 0.4 cm. Color: RHS 145B. Texture: Tomentose.

Flower buds:
*Shape.*—Irregular to oblong.
*Length.*—3.0 cm to 4.5 cm.
*Diameter.*—0.8 cm.
*Color at tight bud.*—RHS 184A.
*Texture.*—Slightly pubescent.

Inflorescence:
*Blooming habit* (*flowering season*).—Permanent flowering during the summertime.
*Inflorescence type.*—Cymose.
*Number of flowers per node.*—2.
*Lastingness of individual blooms on the plant.*—7 to 10 days.
*Fragrance.*—Absent.
*Flowers.*—Arrangement: Composed of 5 petals fused at the base. Shape: Funnel form. Diameter (flower face): 6.5 cm. Depth (total length of flower): 4.8 cm. Throat/Funnel: Length: 2.5 cm. Diameter (at opening): 1.0 cm. Texture (both inner and outer surfaces): Smooth, glabrous.
*Petals.*—Color of petals, immature flower: Upper surface: RHS 44A. Lower surface: RHS N34C to RHS 35A. Color of petals, mature flower: Upper surface: RHS 34A. Lower surface: Between RHS 39B and RHS 39C. Apex: Broadly mucronate. Base: Fused. Margin: Entire. Strength of waviness: Weak. Degree of lobation: Weak. Calyx arrangement: Actinomorphic, composed of 5 sepals.
*Sepals.*—Color: Upper surface: RHS 137A. Lower surface: RHS 146A. Length: 1.0 cm to 1.2 cm. Width: 0.2 cm to 0.3 cm. Shape: Linear. Apex: Acute. Base: Attenuate. Margin: Entire. Texture (both surfaces): Tomentose.
*Pedicels.*—Color: RHS 144A. Length: About 2.0 cm. Diameter: 0.15 cm. Texture: Tomentose.

Reproductive organs:
*Stamens.*—Quantity: 5. Shape: Needle like with elliptic head. Filament: Length: 1.0 cm to 1.3 cm. Diameter: 0.015 cm. Color: RHS 149D. Anther: Shape: Elliptic. Color: RHS 155D. Pollen: Color: RHS 158B. Amount: Moderate.
*Pistils.*—Quantity per flower: 1. Length: 2.0 cm. Stigma color: RHS 144A. Style color: RHS 145C.

Fruit/seed set: None observed.
Disease/insect resistance: None observed.

COMPARISON WITH PARENTAL LINES AND KNOWN VARIETY

'KLEPH14249' is distinguished from its parents as described in Table 1:

TABLE 1

Comparison with Parental Lines

| Trait | Variety 'KLEPH14249' | Female parent Surprise Orange Twist | Male Parent 'PH-2009-1404' |
|---|---|---|---|
| Flower color | Darker orange | Brilliant orange | Red |

'KLEPH 14249' is most similar to the petunia plant commercially known as Surprise Orange Twist (patent status unknown). Differences between the two varieties are described in Table 2:

TABLE 2

Comparison with Similar Variety

| Trait | Variety 'KLEPH14249' | Commercial line Surprise Orange Twist |
|---|---|---|
| Flower color | Darker orange | Brilliant orange |

We claim:

1. A new and distinct variety of *petunia* plant named 'KLEPH 14249' as illustrated and described herein.

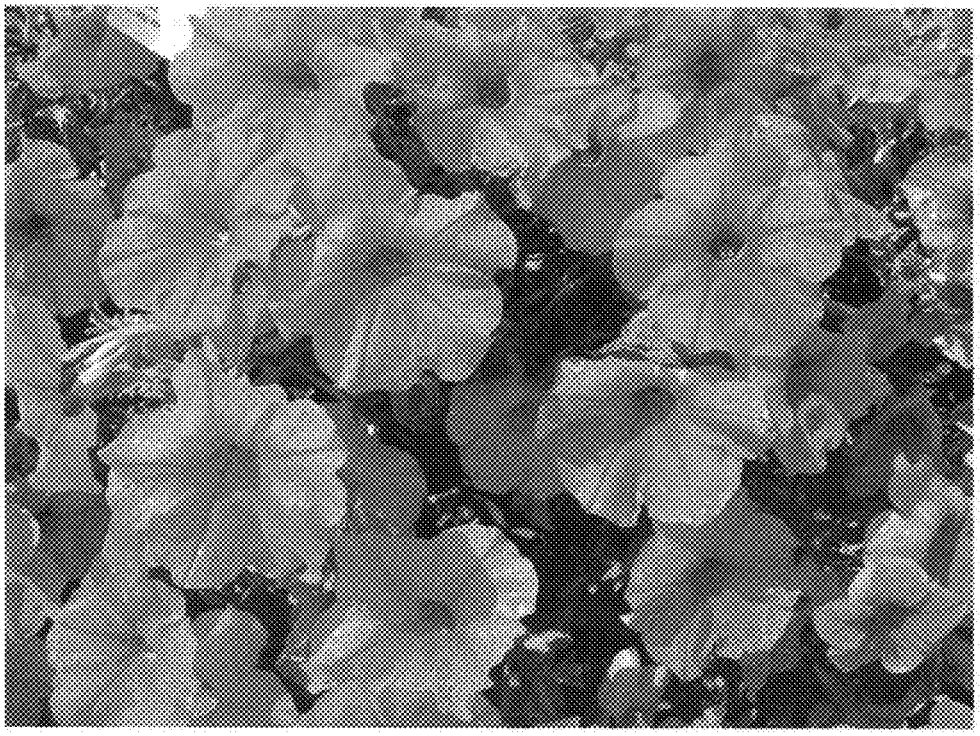

* * * * *